United States Patent [19]

Sarantakis

[11] 4,180,500
[45] * Dec. 25, 1979

[54] POLYPEPTIDES RELATED TO SOMATOSTATIN

[75] Inventor: Dimitrios Sarantakis, West Chester, Pa.

[73] Assignee: American Home Products Corporation, New York, N.Y.

[*] Notice: The portion of the term of this patent subsequent to Mar. 7, 1995, has been disclaimed.

[21] Appl. No.: 851,928

[22] Filed: Nov. 16, 1977

[51] Int. Cl.² .................. C07C 103/52; A61K 37/00
[52] U.S. Cl. ........................ 260/112.5 S; 424/177
[58] Field of Search ............... 260/112.5 S; 424/177

[56] References Cited

U.S. PATENT DOCUMENTS 4,077,952  3/1978  Sarantakis ............... 260/112.5 S

FOREIGN PATENT DOCUMENTS 839405  10/1976  Belgium ..................... 260/112.5 S

OTHER PUBLICATIONS

J. Rivier et al., J. Med. Chem. 18, 123 (1975).
J. Rivier et al., Biochem. Biophys. Res. Commun. 65, 746 (1975).
A. Loffet, Peptides, 1976, pp. 427–451.

*Primary Examiner*—Delbert R. Phillips

[57] ABSTRACT

Polypeptides of the formula:

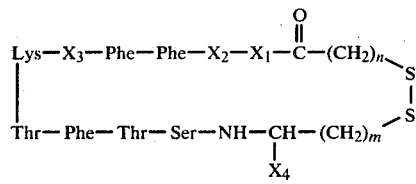

and the reduced linear form thereof, wherein:
$X_1$ is Arg or His;
$X_2$ is His, Tyr, or Glu;
$X_3$ is Trp or D-Trp; or 6-F-D-Trp
$X_4$ is

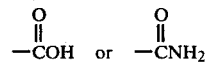

n is 1, 2, 3, or 4; and
m is 1 or 2; or the non-toxic acid addition salts thereof, inhibit the secretion of growth hormone and glucagon without materially affecting the secretion of insulin.

7 Claims, No Drawings

POLYPEPTIDES RELATED TO SOMATOSTATIN

Somatostatin is the cyclic disulfide tetradecapeptide of the formula:

$$\begin{array}{c} \text{H—Ala—Gly—Cys—Lys—Asn—Phe—Phe—Trp} \\ \phantom{xxxxxxx} | \phantom{xxxxxxxxxxxxxxxxxxxxxxxxxx} | \\ \phantom{xxxxxxx} S \phantom{xxxxxxxxxxxxxxxxxxxxxxxxxx} \\ \phantom{xxxxxxx} | \\ \phantom{xxxxxxx} S \\ \phantom{xxxxxxx} \backslash \\ \text{HO—Cys—Ser—Thr—Phe—Thr—Lys} \end{array} \quad \text{I}$$

This peptide (I) has been identified as the "somatotropin-release inhibiting factor" (SRIF) which is secreted by the hypothalamus and regulates the secretion of pituitary growth hormone (GH) (somatotropin). [See Brazeau et al., *Science*, 179, 77 (1973), Burgus et al., *Proc. Nat. Acad. Sci.* (U.S.A.), 70, 684 (1973), and Ling et al., *Biochemical and Biophysical Res. Communication*, 50, 127 (1973)]. The reduced form of somatostatin (RS) is the linear tetradecapeptide of the formula:

$$\text{H—Ala—Gly—Cys(SH)—Lys—Asn—Phe—Phe—Trp—Lys—Thr—Phe—Thr—Ser—Cys(SH)—OH} \quad \text{II}$$

The reduced form (II) has been prepared by total synthesis, [see Rivier et al., *C. R. Acad. Sci. Ser. p. Sci. Natur.* (Paris), 276, 2737 (1973) and Sarantakis and McKinley, *Biochem. and Biophys. Res. Communications*, 54, 234 (1973)] and it (II) can be converted to somatostatin (I) by oxidation whereby a bridging bond is formed between the two sulfhydryls of the two cysteinyl amino acid residues in the tetradecapeptide.

Various polypeptides which may be regarded as structural modifications of somatostatin have been prepared synthetically and are reported in the chemical literature. Such polypeptides have certain structural features in common with somatostatin and differ from somatostatin in that specific amino acid residues or functional groups originally present in the somatostatin molecule are either missing or are replaced by other amino acid residues or functional groups. The present invention relates to novel synthetic biologically active polypeptides which may be regarded as a structural modification of somatostatin. The polypeptides of the invention differ from somatostatin in the following respects: (a) the $\text{Ala}^1\text{-Gly}^2$ segment is missing; (b) the $\text{Cys}^2$ residue is replaced by a ω-mercapto(lower)alkanoic acid residue; (c) the $\text{Lys}^4$ residue is replaced by Arg or His; (d) the $\text{Asn}^5$ residue is replaced by His, Tyr, or Glu; (e) the $\text{Trp}^8$ residue is either present or is replaced by D-Trp or 6-F-D-Trp; and (f) the $\text{Cys}^{14}$ residue is either present or replaced by D-Cys, D-Cys—$NH_2$, Homo-Cys, D-Homo-Cys, Homo-Cys—$NH_2$, or D-Homo-Cys—$NH_2$. Modifications of somatostatin missing the $\text{Ala}^1\text{-Gly}^2$ segment and the N-terminal amino group are reported by Rivier et al., *J. Med. Chem.*, 18, 123 (1975). Replacement of the $\text{Trp}^8$ residue by D-Trp is discussed by Rivier et al., *Biochem. Biophys. Res. Commun.*, 65, 746 (1975). Modifications of somatostatin wherein the $\text{Lys}^4\text{-Asn}^5$ segment are replaced with other amino acid residues are disclosed in Belgian Pat. No. 839,405.

The invention sought to be patented comprises a chemical compound of Formula III:

$$\begin{array}{c} \text{Lys—X}_3\text{—Phe—Phe—X}_2\text{—X}_1\text{—C(=O)—(CH}_2)_n \\ | \phantom{xxxxxxxxxxxxxxxxxxxxxxxxxxxxxxxxxxx} \backslash \\ | \phantom{xxxxxxxxxxxxxxxxxxxxxxxxxxxxxxxxxxxx} S \\ | \phantom{xxxxxxxxxxxxxxxxxxxxxxxxxxxxxxxxxxxx} | \\ | \phantom{xxxxxxxxxxxxxxxxxxxxxxxxxxxxxxxxxxxx} S \\ \text{Thr—Phe—Thr—Ser—NH—CH(X}_4)\text{—(CH}_2)_m / \end{array} \quad \text{III}$$

wherein:
$X_1$ is Arg or His;
$X_2$ is His, Tyr, or Glu;
$X_3$ is Trp or D-Trp; or 6-F-D-Trp
$X_4$ is $$-\text{COH (=O)} \quad \text{or} \quad -\text{CNH}_2 \text{(=O)};$$

n is 1, 2, 3, or 4; and
m is 1 or 2; or
a non-toxic acid addition salt thereof.

In addition the invention contemplates the linear form of the compounds of Formula III, i.e. the non-cyclic reduced compounds of Formula IV which contain two free sulfhydryl groups; or a non-toxic acid addition salt thereof.

$$\begin{array}{c} \text{Lys—X}_3\text{—Phe—Phe—X}_2\text{—X}_1\text{—C(=O)—(CH}_2)_n\text{—SH} \\ | \\ \text{Thr—Phe—Thr—Ser—NH—CH(X}_4)\text{—(CH}_2)_m\text{—SH} \end{array} \quad \text{IV}$$

All optically active amino acids herein described and all amino acid residues in the polypeptides of Formula III and IV and the other polypeptides herein described are in the natural or L-configuration, unless otherwise indicated.

It will be apparent to those skilled in the art that the carbon atom to which is attached the group represented by $X_4$ is assymetric and therefore the configuration at the carbon can be in either the L- or D-form.

The compounds of Formula III and the linear reduced form thereof (Formula IV) inhibit the secretions of growth hormone and glucagon, without materially affecting the secretion of insulin, and, therefore, are useful in controlling serum glucose in the treatment of diabetes. The compounds can be administered either alone or in combination with insulin.

Preferred compounds of Formula III and IV are those wherein:
(a) $X_1$ is Arg; $X_2$ is His; $X_3$ is D-Trp; $X_4$ is —$CO_2H$; n is 2; and m is 1;
(b) $X_1$ is Arg; $X_2$ is Glu; $X_3$ is D-Trp; $X_4$ is —$CO_2H$; n is 2; and m is 1; and
(c) $X_1$ is His; $X_2$ is His; $X_3$ is D-Trp; $X_4$ is —$CO_2H$; n is 2; and m is 1.

The preparation of the above embodiments is described in the Examples. The Examples will illustrate the preparative methods applicable to the production of other embodiments. A desired embodiment can be prepared using the described technique by substituting a desired protected amino acid or δ-mercapto(lower)-alkanoic acid for a particular moiety illustrated in the Examples.

In general, the polypeptides of this invention are produced by the well known solid phase method as described by Stewart et al., Solid Phase Peptide Synthesis, Freeman and Co., San Francisco, 1969. As applied to the compounds of this invention, α-amino and sulfhydryl protected cysteine or homocysteine is attached to a chloromethylated polystyrene resin and the α-amino protecting group is then removed with trifluoroacetic acid in methylene chloride, trifluoroacetic acid alone or hydrogen chloride in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., *Analyt. Biochem.*, 34, 595 (1970). Where incomplete coupling has occurred, the reaction is repeated before the α-amino protecting group is removed for introduction of the next amino acid sequence. Dicyclohexylcarbodiimide was employed as the coupling reagent.

After the desired amino acid sequence has been synthesized, the polypeptide is removed from the resin support by treatment with hydrogen fluoride and anisole to obtain the fully deprotected linear polypeptide. The cyclic disulfide is produced by oxidation, such as by treatment with $K_4Fe(CN)_6$ or by contact with air.

Non-toxic acid addition salts of the linear and cyclic polypeptides are produced by methods well known in the art from organic or inorganic acids which are non-toxic and acceptable for pharmaceutical purposes, such as hydrochloric, hydrobromic, sulfuric, phosphoric, polyphosphoric, maleic, acetic, citric, benzoic, succinic, malonic, or ascorbic acid and the like.

The protecting groups employed throughout the solid phase synthesis are well known to the art. In selecting a particular side chain protecting group to be used in the synthesis of the peptides of this invention, the following rules should be followed: (a) the side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The compounds of Formula III and IV wherein $X_4$ is $-NH_2$ are made by removing the polypeptide from the resin support by treatment of ammonia.

As used herein, "6-F-D-Trp" means D-tryptophan in which the 6-position is substituted by fluorine.

The processes of the invention are illustrated in the following Examples:

EXAMPLE 1 s-p-Methoxybenzyl-β-mercaptopropionyl-$N^g$-tosyl-L-arginyl-$N^{im}$-tosyl-L-histidyl-L-phenylalanyl-L-phenylalanyl-D-tryptophyl-$N^\epsilon$-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl hydroxymethyl polystyrene ester Chloromethylated polystyrene resin was esterified with Boc-Cys(SMBzl)-OH according to Gisin, *Helv. Chim. Acta*, 56, 1976 (1973) and the polymeric ester was treated according to Schedule A for the incorporation of Boc-Ser(Bzl)-OH, Boc-Thr(Bzl)-OH, Boc-Phe-OH, Boc-Thr(Bzl)-OH, Boc-Lys(ClZ)-OH, Boc-D-Trp-OH, Boc-Phe-OH, Boc-Phe-OH, Boc-His(Tos)-OH, Boc-Arg(TOS)OH, and MPA(SMBzl)-OH), (S-p-methoxybenzyl-β-metcaptopropionic acid).

Schedule A

1. Wash with $CH_2Cl_2 \times 3$.
2. Treat with TFA-$CH_2Cl_2$-EDT (1:1:5%, v/v) for 5 min.
3. Treat as in 2 for 25 min.
4. Wash with $CH_2CL_2 \times 3$.
5. Wash with DMF.
6. Treat with 12% in DMF twice for 3 min.
7. Wash with DMF.
8. Wash with $CH_2CL_2 \times 3$.
9. Treat with 4 equivalents of the corresponding amino acid derivative in $CH_2CL_2$-DMF and stir for 5 min.
10. Add in two portions 5 equivalents of DIC dissolved in $CH_2Cl_2$ and over a period of 30 min. Reaction time 6 hours.
11. Wash with DMF×3.
12. Wash with $CH_2Cl_2 \times 3$.
13. Test ninhydrin reaction according to Kaiser et al., *Annal. Biochem.*, 34, 595 (1970). In case of incomplete reaction repeat lines 9 to 13 as above.

EXAMPLE 2

β-Mercaptopropionyl-L-arginyl-L-histidyl-L-phenylalanyl-L-phenylalanyl-D-tryptophyl-L-lysyl-L-threonyl-L-phenylalanyl-L-threonyl-L-seryl-L-cysteine cyclic (1–11)disulfide The peptido resin of the previous example (9.2 g.) was mixed with anisole (18 ml.) and treated with liquid HF in an ice bath and with exclusion of air, for one hour. The excess HF was removed in vacuo as fast as possible (ca. 45 minutes) and the residue was treated with deaerated 2 N-aqueous acetic acid and filtered. The filtrate was extracted with ether and the aqueous phase was diluted to 8 liters with deaerated water then the pH was adjusted to 7 with dilute $NH_4OH$ and the compound was oxidized with a solution of $K_3Fe(CN)_6$ (1.5 g. in 500 ml. water). The excess reagent and $K_4Fe(CN)_6$ was removed with BioRad AG3 after acidification of the solution to pH 5 with glacial acetic acid. The peptidic material was absorbed onto a column of Amberlite CG 50 and then eluted with 30% aqueous acetic acid. The fractions containing peptidic material were pooled and lyophilized to yield 720 mg. of crude product. This crude material was applied onto a column of Sephadex G 15 (2.3×153 cm) and eluted with 10% aqueous acetic acid. The material which emerged in fractions (5.1 ml. each) 92 to 120 was pooled and lyophilized to yield the title peptide as the triacetate salt, 186 mg. TLC, BWA, 4:1:1, Rf=0.5, BWA, 4:5:1, Rf 0.53, BWAP, 30:24:6:20, Rf 0.60. Amino acid analysis: Thr (2) 191, Ser (1) 0.91, Cys (2) 1.07, Phe (3) 3, Lys (1) 1.03, His (1) 0.99, Trp (1) 0.81, Arg (1) 0.99.

EXAMPLE 3

β-Mercaptopropionyl-L-arginyl-L-glutamyl-L-phenylalanyl-L-phenylalanyl-D-tryptophyl-L-lysyl-L-threonyl-L-phenylalanyl-L-threonyl-L-seryl-L-cysteine cyclic (1–11) disulfide The peptido resin, MPA (SMBzl)-Arg(Tos)-Glu(OBzl)-Phe-Phe-D-Trp-Lys(ClZ)-Thr(Bzl)-Phe-Thr(Bzl)-Ser(Bzl)-Cys(SMBzl)-O-Resin was prepared in a fashion similar to Example 1. The above peptido resin (8.5 g.) was mixed with anisole (17 ml.) and treated with liquid HF in an ice bath for 60 minutes. The excess HF was removed in vacuo as fast as possible ca. 45 minutes) and the residue was extracted with 2 M aq. acetic acid. The filtrate was poured into 75 liters of deaerated water and the pH was adjusted to 7.2 with dilute $NH_4OH$. The solution was stirred overnight in the open air then acidified to pH 5 with gl. acetic acid and the peptide was absorbed onto Amberlite CG 50 ($H^+$ form). The peptidic material was eluted with 50% aq. acetic acid and lyophilized to yield 823 mg. crude product. This crude product was chromatographed through a column of Sephadex G-25 which was eluted with 10% aq. acetic acid to afford 232 mg. of the title compound as the diacetate salt. TLC, Avicel prewashed plates, chlorox spray: Rf (BWA, 4:5:1, v/v) 0.62, Rf (BWA, 4:1:1, v/v) 0.72, Rf (tAmOH-P-W, 7:7:6, v/v) 0.77. Amino acid analysis: Thr (2) 1.82, Ser (1) 0.56, Glu (1) 1.18, Phe (3) 3, Trp (1) 0.86, Arg (1) 1.05, Cys, N.D.

EXAMPLE 4

β-Mercaptopropionyl-L-histidyl-L-histidyl-L-phenylalanyl-L-phenylalanyl-D-tryptophyl-L-lysyl-L-threonyl-L-phenylalanyl-L-threonyl-L-seryl-L-cysteine cyclic (1–11) disulfide The title compound, as the triacetate salt, was prepared in a fashion similar to Example 3 and was purified by chromatography through Sephadex G 25 followed by Sephadex G 15. TLC, Avicel prewashed glass plates, chlorox spray: Rf (BWA, 4:1:1, v/v) 0.53, Rf (tAmOH-P-W, 7:7:6, v/v) 0.76. Amino acid analysis: Thr (2) 1.87, Phe (3) 3, Lys (1) 1.04, His (2) 1.63, Trp (1) 0.74, Cys, N.D.

EXAMPLE 5

The biological activity of the products of the preceding preparatory examples were determined by the following procedure:

Albino male rats were administered Nembutal intraperitoneally at a dose of 50 milligrams per kilogram. Fifteen minutes later a subcutaneous injection of the test compound of physiological saline was administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot was assayed for growth hormone (GH), insulin and glucagon by radio immunoassay. The results of the assay are as follows:

| Compound | Dose ug/kg | GH ng/kg | Insulin μU/ml | Glucagon pg/ml | No. of Animals |
|---|---|---|---|---|---|
| Control | — | 220 ± 32 | 372 ± 56 | 39 ± 13 | 10 |
| Example 2 | 200 | 33 ± 8* | 253 ± 53 | 0 ± 0* | 10 |
| Control | — | 180 ± 23 | 321 ± 31 | 72 ± 11 | 10 |
| Example 3 | 200 | 70 ± 5* | 236 ± 32 | 29 ± 7* | 10 |
| Control | — | 350 ± 67 | 358 ± 53 | 79 ± 25 | 10 |
| Example 4 | 200 | 140 ± 22* | 394 ± 82 | 23 ± 6+ | 10 |

*$p<0.01$
+$p<0.05$

The above compounds were also tested for their duration of effect on growth hormone secretion in rats treated with Nembutal. Blood samples were obtained by cardiac puncture and plasma separated for radioimmunoassay of GH concentration. The results of testing for long-acting activity are as follows:

| Compound | Dose ug/kg | Growth Hormone ng/ml | Time hrs. | No. of Animals |
|---|---|---|---|---|
| Control | — | 257 ± 50 | 2 | 9 |
| Example 2 | 1000 | 120 ± 19⁻ | 2 | 9 |
| Control | — | 205 ± 35 | 4 | 9 |
| Example 2 | 1000 | 183 ± 33 | 4 | 9 |
| Control | — | 428 ± 104 | 2 | 9 |
| Example 3 | 1000 | 106 ± 16* | 2 | 9 |
| Control | — | 209 ± 28 | 4 | 9 |
| Example 3 | 1000 | 87 ± 22* | 4 | 9 |
| Control | — | 280 ± 40 | 2 | 10 |
| Example 4 | 1000 | 202 ± 19 | 2 | 9 |
| Control | — | 254 ± 27 | 4 | 10 |
| Example 4 | 1000 | 247 ± 51 | 4 | 9 |

⁻$p<0.05$
*$p<0.01$

The data show that the compounds of Examples 2, 3, and 4, representative of the other compounds of the invention, are effective agents for reducing secretion of growth hormone and glucagon without materially affecting insulin levels at a dose of 200 g/kg. The results also indicate that the compounds of Examples 2 and 3 show long-acting inhibition of growth-hormone release.

The compounds described herein may be administered to warm-blooded mammals, either intravenously, subcutaneously, intramuscularly, or orally to control serum glucose in the treatment of diabetes. The required dosage will vary with the particular condition being treated, the severity of the condition and the duration of treatment.

The active ingredient may be administered alone or in combination with pharmaceutically acceptable carriers or excipients. Suitable pharmaceutical compositions will be apparent to those skilled in the art.

What is claimed is:

1. A chemical compound of the formula:

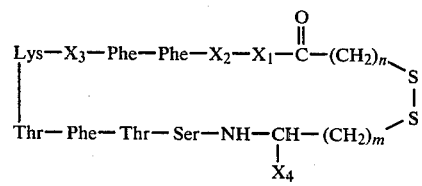

wherein:
$X_1$ is Arg or His;
$X_2$ is His, Tyr, or Glu;
$X_3$ is Trp or D-Trp; or 6-F-D-Trp $X_4$ is

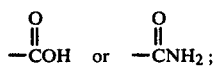

n is 1, 2, 3, or 4; and
m is 1 or 2;
or the reduced linear form thereof; or a non-toxic pharmaceutically acceptable acid addition salt thereof.

2. A compound as defined in claim 1 which is β-mercaptopropionyl-L-arginyl-L-histidyl-L-phenylalanyl-L-phenylalanyl-D-tryptophyl-L-lysyl-L-threonyl-L-phenylalanyl-L-threonyl-L-seryl-L-cysteine.

3. A compound as defined in claim 1 which is β-mercaptopropionyl-L-arginyl-L-histidyl-L-phenylalanyl-L-phenylalanyl-D-tryptophyl-L-lysyl-L-threonyl-L-phenylalanyl-L-threonyl-L-seryl-L-cysteine cyclic (1-11) disulfide.

4. A compound as defined in claim 1 which is β-mercaptopropionyl-L-arginyl-L-glutamyl-L-phenylalanyl-L-phenylalanyl-D-tryptophyl-L-lysyl-L-threonyl-L-phenylalanyl-L-threonyl-L-seryl-L-cysteine.

5. A compound as defined in claim 1 which is β-mercaptopropionyl-L-arginyl-L-glutamyl-L-phenylalanyl-L-phenylalanyl-D-tryptophyl-L-lysyl-L-threonyl-L-phenylalanyl-L-threonyl-L-seryl-L-cysteine cyclic (1-11) disulfide.

6. A compound as defined in claim 1 which is β-mercaptopropionyl-L-histidyl-L-histidyl-L-phenylalanyl-L-phenylalanyl-D-tryptophyl-L-lysyl-L-threonyl-L-phenylalanyl-L-threonyl-L-seryl-L-cysteine.

7. A compound as defined in claim 1 which is β-mercaptopropionyl-L-histidyl-L-histidyl-L-phenylalanyl-L-phenylalanyl-D-tryptophyl-L-lysyl-L-threonyl-L-phenylalanyl-L-threonyl-L-seryl-L-cysteine cyclic (1-11) disulfide.

* * * * *